United States Patent [19]

Foster

[11] 4,067,922
[45] Jan. 10, 1978

[54] LITHIUM FERRITE CATALYSED OXIDATIVE DEHYDROGENATION PROCESS

[75] Inventor: Alan W. Foster, Houston, Tex.

[73] Assignee: Petro-Tex Chemical Corporation, Houston, Tex.

[21] Appl. No.: 700,575

[22] Filed: June 28, 1976

Related U.S. Application Data

[62] Division of Ser. No. 578,538, May 19, 1975, Pat. No. 3,998,757.

[51] Int. Cl.² .............................................. C07C 11/12
[52] U.S. Cl. .......................... 260/680 E; 260/668 D; 260/683.3
[58] Field of Search ............ 260/680 E, 668 D, 683.3; 252/62.61, 470, 474, 465

[56] References Cited

U.S. PATENT DOCUMENTS

| | | | |
|---|---|---|---|
| 3,686,347 | 8/1972 | Dean et al. | 260/680 E |
| 3,843,745 | 10/1974 | Christman et al. | 260/680 E |
| 3,845,153 | 10/1974 | Croce et al. | 260/680 E |
| 3,998,757 | 12/1976 | Foster | 252/465 |

Primary Examiner—O. R. Vertiz
Assistant Examiner—Brian E. Hearn
Attorney, Agent, or Firm—Kenneth H. Johnson

[57] ABSTRACT

Oxidative dehydrogenation catalysts containing lithium, iron and oxygen, with or without aluminum or chromium, and containing the corresponding ferrite, give superior results and operate at generally lower temperatures than many other ferrite oxidative dehydrogenation catalysts.

11 Claims, No Drawings

LITHIUM FERRITE CATALYSED OXIDATIVE DEHYDROGENATION PROCESS

This is a division, of application Ser. No. 578,538 filed May 19, 1975, now U.S. Pat. No. 3,998,757.

BACKGROUND OF THE INVENTION

The present invention relates to oxidative dehydrogenation catalysts containing lithium iron and oxygen and the process of oxidative dehydrogenation using these catalysts. More particularly, the catalysts are ferrites.

Oxidative dehydrogenations employing ferrite catalysts are well known. U.S. Pat. Nos. 3,270,080; 3,284,536; 3,303,234; 3,303,235; 3,303,236; 3,303,238; 3,308,182; 3,324,195; 3,334,152; 3,342,890; 3,398,100; 3,450,787; 3,420,911; 3,420,912; 3,428,703 and 3,440,299 disclose such processes.

Some prophetic disclosures concerning ferrites tended to regard lithium equivalent to a number of other metals in forming ferrites useful for oxidative dehydrogenation, e.g., U.S. Pat. Nos. 3,666,684; 3,670,042; 3,686,347; 3,702,875; 3,743,683; 3,751,512; 3,780,126 and 3,843,745, which all contain substantially the same disclosure in regard to lithium.

In the present application which deals specifically with the lithium ferrite species critical perimeters and combinations have been discovered, which were not considered, investigated, noted, or suggested by the prior art.

SUMMARY OF THE INVENTION

This invention relates to novel oxidation dehydrogenation catalysts and the process of oxidative dehydrogenation using the catalysts. Briefly, the catalyst composition for use in oxidative dehydrogenation which consist essentially of lithium, iron and oxygen, wherein the mole ratio of lithium to iron is between 2/5 and 1/7, preferably about ¼ to 1/6, or about 1/5 to 1/5.5, and the surface area of the catalyst is greater than 8.1 m²/gram, preferably 10.5 m²/gram or more. Normally the surface area of the catalyst will not exceed about 200 m²/gram. Aluminum and/or chromium may be substituted for a portion of the iron. Up to about 48 mole %, preferably about 40 mole %, of the iron may be replaced with $Al^{+++}$ or $Cr^{+++}$ and have substantially the same catalyst activity, but at lower inlet temperatures.

DETAILED DESCRIPTION OF THE INVENTION

The catalyst of the present invention contain lithium, iron, and oxygen or lithium, iron, oxygen, and aluminum or chromium as described above. The iron and any aluminum or chromium substituted in the composition for iron has a +3 valence. The catalyst of the present invention comprise ferrites which are spinel crystalline compositions of the lithium, iron, oxygen, and aluminum or chromium. A preferred catalyst of this type is that having a face-centered cubic form of crystalline structure.

Lithium and iron form binary spinels of the $Li_{1/2}^+ Fe_{5/2}^{+++}O_4$. Similarly, aluminum and chromium form these compounds with lithium and iron.

In the close-packed array of oxygen ions of the cubic spinel in the structure (which derives its name from the mineral $MgAl_2O_4$) two types of interstitial sites occur: tetrahedral and octahedral, there being 64 and 32 sites, respectively, of which only 8 and 16, respectively are occupied. The tetrahedral sites are relatively small and generally will not provide sufficient space for the metal ions without expanding the site. This expansion is accomplished in the spinel by a displacement of the four oxygen ions away from the metal ions along the body diagonals of the octants having central metal ions. Whereas, the oxygen ions in the "octahedral octant" are displaced in such a way that this oxygen tetrahedron shrinks by the same amount as the metal tetrahedron expands. Thus, cubic symmetry is preserved.

It has been found that some other metals which form binary compounds of the spinel structure are not suitable or equivalent in the present compositions to the listed metals. For example, Na and K are not suitable substitutes for Li and produce inactive catalysts. Similarly, $Cu^{+1}$ decreases the activity of the catalysts.

Ferrite formation may be accomplished by reacting an active compound or iron with an active compound of the designated metals. By active compound is meant a compound which is reactive under the conditions to form the ferrite, generally oxides, hydroxides or salts. Starting compounds of iron or the other metals may be such as the nitrates, hydroxides, hydrates, oxalates, carbonates, acetates, formates, halides, oxides, etc. The starting compounds are suitably oxides, or compounds which will decompose to oxides during the formation of the ferrite such as organic salts and inorganic salts or hydroxides. For example, lithium oxalate may be reacted with iron oxide hydrates to form lithium ferrite. Salts of the desired metals may be coprecipitated and the precipitate heated to form the ferrite. Desired ferrites may be obtained by conducting the reaction to form the ferrite at relatively low temperatures, that is, at temperatures lower than some of the very high temperatures used for the formation of some of the semi-conductor application. Good results, e.g., have been obtained by heating the ingredients to a temperature high enough to produce the required ferrite, but a conditions no more severe than equivalent to heating at 950° C or 1000° C for 90 minutes in air and generally the maximum temperature will be less than 1300° C and preferably less than 1150° C. Methods adapted for preparing catalysts suitable for this invention are disclosed in U.S. Pat. Nos. 3,270,080; 3,284,536; 3,303,234–6; 3,303,238; 3,308,182; 3,334,152; 3,342,890; 3,686,347; 3,450,787; and, 3,843,745 and these disclosures are hereby incorporated by reference.

The catalyst compositions may contain an excess of either iron or lithium over the stoichiometric amount to form the ferrite. Furthermore, there may be unreacted lithium ferrite precursors present in the compositions in addition to the ferrite.

The present catalyst compositions have been found to exhibit a certain type of X-ray diffraction pattern. The compositions do not have any sharp X-ray diffraction reflection peaks as would be found, e.g., in a highly crystalline material having the same chemical composition. Instead, the compositions of this invention exhibit reflection peaks which are relatively broad. The degree of sharpness of the reflection peak may be measured by the reflection peak bank width at half height (Wh/2). In other words, the width of the reflection peak as measured at one half of the distance to the top of the peak is the "band width at half height". The band width at half height is measured in units of °2 theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.16° 2 theta and normally will be at least 0.20° 2 theta. For instance, excellent compositions have been made with band widths at half height of at least 0.22° or 0.23° 2 theta. The particular reflection peak used to measure the band width at one-half height is the reflection peak having Miller (hkl) indices of 220. (See, e.g., Chapter of Klug and Alexander, ibid). Applicants do not wish to be limited to any theory of the invention in regard to the relationship between composition activity and band width. The catalyst composition may also include inert binding agents and carriers or supports for the catalyst, such as alumina, pumice, silica and so forth, but these will not ordinarily exceed about 80 percent or 90 percent by weight of the catalytic composition including active catalyst components and inert binding agents or fillers. The catalyst will be by definition present in a catalytic amount. The amount of catalyst ordinarily will be greater than ten square feet of catalyst surface per cubic foot of reaction zone containing catalyst. The term "catalysts", as used herein, means total active catalyst components and does not include inert binding agents or fillers. Of course, the amount of catalyst may be much greater, particularly, when irregular surface catalyst is used. When the catalyst is in the form of particles, either supported or unsupported, the amount of catalyst surface may be expressed in terms of the surface area per unit weight. The ratio of catalyst surface to weight will be dependent upon several factors, including the particle size distribution, apparent bulk density of the particles, the carrier, etc. Stated otherwise, the compositions referred to in this application are the main active constituents of the dehydrogenation process during dehydrogenation and any ratios and percentages refer to the surface of the catalyst in contact with the gaseous phase during dehydrogenation.

The compositions of this invention may also comprise additives, such as disclosed in U.S. Pat. No. 3,270,080 and U.S. Pat. No. 3,303,238. Phosphorus, silicon, boron, sulfur, or mixtures thereof are examples of additives. These additives are added to the preformed ferrites usually by slurrying the ferrite and the additive, such as phosphoric acid, in the desired ratio. Polyvinyl alcohol may be advantageously employed in forming the catalyst into useable configurations such as extruded pellets.

The catalysts may be activated or regenerated by reducing with a reducing gas, e.g., such as hydrogen or hydrocarbons. For example, the preformed compositions may be reduced with, e.g., hydrogen at a temperature of at least 250° C with the temperature of reduction generally being no greater than 850° C. The period of time for reduction will be dependent somewhat on the temperature of reduction.

The process of this invention may be applied to the dehydrogenation of a wide variety of organic compounds. Such compounds normally will have from 2 to 20 carbon atoms, at least one

grouping, a boiling point below about 350° C, and such compounds may contain other elements, in addition to carbon and hydrogen such as oxygen, halogens, nitrogen and sulfur. A preferred group of organic reactants are hydrocarbons. Preferred are compounds having 2 to 12 carbon atoms, and especially preferred are compounds of 3 to 6 or 8 carbon atoms.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustration of dehydrogenations include propionitrile to acrylonitrile; propionaldehyde to acrolein; ethyl chloride to vinyl chloride; methyl isobutyrate to methyl methacrylate; 2 or 3 chlorobutene-1 or 2; 2, 3-dichlorobutane to chloroprene; ethyl pyridine to vinyl pyridine; ethylbenzene to styrene; isopropylbenzene to α-methyl styrene; ethylcyclohexane to styrene; cyclohexane to benzene; ethane to ethylene or acetylene; propane to propylene, methyl acetylene, allene, or benzene; isobutane to isobutylene; n-butane to butene and butadiene-1, 3; n-butene to butadiene-1, 3, and vinyl acetylene; methyl butene to isprene; cyclopentane to cyclopentene and cyclopentadiene; n-octane to ethyl benzene and ortho-xylene; monomethylheptanes to xylenes; ethyl acetate to vinyl acetate; 2, 4, 4-trimethylpentane to xylenes; and the like. Some representative materials which may be dehydrogenated by the novel process of this invention include ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1, 3 dichlorobutane, 1,4 dichlorobutane, the chlorofluoroethanes, methyl pentane, methylethyl ketone, diethyl ketone; n-butyl alcohol, methyl propionate and the like.

Illustrative dehydrogenation reactions are the following: Acyclic compounds having 4 to 5 contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2, 4, 4-trimethylpentene-1 to a mixture of xylenes; acyclic compounds having 6 to 16 carbon atoms and no quaternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

The preferred compounds to be dehydrogenated are hydrocarbons with a particularly preferred class being acyclic hydrocarbons having 4 to 5 contiguous carbon atoms or ethyl benzene and the preferred products are butene-1 or 2, butadiene-1, 3, vinyl acetylene, 2-methyl-1-butene, 3-methyl-1-butene, 2-methyl-2-butene, isoprene, styrene or mixtures thereof. Especially preferred as feed are butene-1 or 2 and the methyl butenes and mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about or in excess of atmospheric pressure, although sub-atmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

The organic compound to be dehydrogenated is contacted with oxygen in order for the oxygen to oxidatively dehydrogenate the compound. Oxygen may be fed to the reactor as pure oxygen, as air, as oxygen-enriched air, oxygen mixed with diluents, solid oxidants, and so forth. Oxygen may also be added in increments to the dehydrogenation zone. Although determinations regarding the mechanism of reaction are difficult, the process of this invention is an oxidative dehydrogenation process wherein the apparent mechanism of this invention is the reaction of oxygen with hydrogen released from the hydrocarbon.

The amount of oxygen employed may vary depending upon the desired result such as conversion, selectivity and the number of hydrogen atoms being removed. Thus, to dehydrogenate butane to butene requires less oxygen than does the reaction that proceeds to produce butadiene. Normally, oxygen will be supplied (including all sources, e.g., air to the reactor) in the dehydrogenation zone in an amount from about 0.2 to 1.5, preferably 0.3 to 1.2, mols per mol of $H_2$ being liberated from the organic compound. Ordinarily the mols of oxygen supplied will be in the range of from .2 to 2.0 mols per mol of organic compound to be dehydrogenated and for most dehydrogenations this will be within the range of .25 to 1.5 mols of oxygen per mol of organic compound.

Preferably, the reaction mixture contains a quantity of steam or diluent such as nitrogen with the range generally being between about 2 and 40 mols of steam per mol of organic compound to be dehydrogenated. Preferably, steam will be present in an amount from about 3 to 35 mols per mol of organic compound to be dehydrogenated and excellent results have been obtained within the range of about 5 to about 30 mols of steam per mol of organic compound to be dehydrogenated. The functions of the steam are several-fold, and the steam may not merely act as a diluent. Diluents generally may be used in the same quantities as specified for the steam. These gases serve also to reduce the partial pressure of the organic compound.

Halogen may also be present in the reaction gases to give excellent results. The presence of halogen in the dehydrogenation zone is particularly effective when the compound to be dehydrogenated is saturated, such as a saturated hydrocarbon. The halogen present in the dehydrogenation zone may be either elemental halogen or any compound of halogen which would liberate halogen under the conditions of reaction. Suitable sources of halogen are such as hydrogen iodide, hydrogen bromide and hydrogen chloride; aliphatic halides, such as ethyl iodide, methyl bromide, methyl chloride, 1, 2-dibromo ethane, cycloaliphatic halides, ammonium iodide, ammonium bromide; ammonium chloride, sulfuryl chloride; and the like. The amount of halogen, calculated as elemental halogen, may be as little as about 0.0001 or less mol of halogen per mol of the organic compound to be dehydrogenated to as high as 0.2 or 0.5.

The temperature for the dehydrogenation reaction generally will be at least about 200° C, such as greater than about 250° C or 275° C, and the maximum temperature in the reactor may be about 700° C or 800° C or perhaps higher such as 900° C under certain circumstances. However, excellent results are obtained within the range of or about 250° C to 600° C, such as from or about 300° C to or about 500° C. The temperatures are measured at the maximum temperature in the dehydrogenation zone.

The gaseous reactants may be conducted through the reaction chamber at a fairly wide range of flow rates. The optimum flow rate will be dependent upon such variables as the temperature of reaction, pressure, particle size, and so forth. Desirable flow rates may be established by one skilled in the art. Generally, the flow rates will be within the range of about 0.10 to 10 liquid volumes of the organic compound to be dehydrogenated per volume of dehydrogenation zone containing catalyst per hour (referred to as LHSV). Usually, the LHSV will be between 0.15 and about 5. for calculation, the volume of a fixed bed dehydrogenation zone containing catalyst is that original void volume of reactor space containing catalyst.

The process of this invention utilizes either a fixed bed or moving bed, such as a fluidized catalyst, reactor. Reactors which have been used for the dehydrogenation of hydrocarbons by non-oxidative dehydrogenation are satisfactory such as the reactors for the dehydrogenation of n-butene to butadiene-1, 3. Although means to remove heat from the reactor may be employed, such as coils, the invention is particularly useful with essentially adiabatic reactors where heat removal is a problem.

The following examples are only illustrative of the invention and are not intended to limit the invention. All percentages are weight percent unless specified otherwise. All conversions (C), selectivities (S) and yields (Y) are expressed in mol percent of the designated feed.

In all of examples 1–19 encompassing the invention as disclosed, the presence of lithium ferrite was determined by X-ray analysis,* ferro magnetism, color change or a combination of these.

* Klug and Alexander, supra. The powder diffraction patterns may be made, with a Norelco constant potential diffraction unit type No. 12215/0 equipped with a wide range goniometer type No. 42273/0 cobalt tube type No. 32119, proportional counter type No. 57250/1; all coupled to the Norelco circuit panel type No. 12206/53. The cobalt K alpha radiation is supplied by operating the tube at a constant potential of 30 kilovolts and a current of 10 milliamperes. An iron filter is used to remove K beta radiation. The detector voltage is 1160 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of ¼° per minute, time constant of 4 seconds and a full scale of $10^3$ counts per second. No correction is made for K α doublet or instrumental broadening of the band widths.

EXAMPLES 1 – 5

In these first runs the effectiveness of lithium ferrite as an oxidative dehydrogenation catalyst (butene-2 to yield butadiene) is demonstrated. A second discovery from these runs was the catalysts having surface areas of 8.1 or less are inferior or inoperable. Catalysts having surface area of 8.1 m²/g. or less and otherwise comparable to those having greater surface area are active, but are unstable and have very short useful lives. The catalysts in these examples were prepared by slurrying $Fe_2O_3.H_2O/Li_2C_2O_4$ in water drying at about 100° C for about 16 hours and calcining for two hours in air (100 ml/min.) and were supported on 7–9 mesh AMC alumina by slurrying the alumina (60%) and actives (38.8%) with $H_3PO_4$ (1.2%). The feed for oxidative dehydrogenation was 98%+butene-2 to produce butadiene (Bd). It should be appreciated by those of skill in the art that the selection of high purity butene-2 to produce butadiene is not a restriction on the operable feeds or the products in the process, but was made, for example, to provide comparable results, availability, calibration of analytical equipment, and standardization of analytical procedures. The ratio of hydrocarbon (butene-2) to oxygen to steam for each example was 1/0.55/15 and the LHSV was 1.5.

The apparatus employed was a one inch Vycor reactor, into which 25 cc of catalyst was placed, equipped with a receiving flask and condenser and heated with a cylindrical furnace assembly. Steam, butene-2 and air are mixed in the reactor head and brought up to the desired temperature in the upper portion of the reactor (which contained about 13 inches of quartz chips). The 25 cc catalyst bed was supported on about 3 inches of quartz chips. Temperatures in the reactor were determined by thermocouples. Table I provides additional information on catalyst and operating conditions and sets forth the results.

rite are set out in Table IV. Note the low inlet temperatures.

TABLE III

Oxidative Dehydrogenation of Butene-2 Over $(Li\ 0.5)\ (Fe_yAl_{2.5-y})O_4$*

| Example No. | Catalysts mole % Al* | "y" | Process Conditions $T_i$ (° C) | $T_{max}$ (° C) | Results C/S/$Y_{Bd.}$ |
|---|---|---|---|---|---|
| 10. | 20 | 2.0 | 292 | 475 | 58/94/55 |
| 11. | 40 | 1.5 | 297 | 478 | 60/94/56 |
| 12. | 60 | 1.0 | 376 | 485 | 53/92/49 |

*Based of Fe replaced.
*Catalysts were prepared by calcining $Fe_2O_3 . H_2O/Li_2C_2O_4/Al(OH)_3$, blends for two hours in air at 600° C. All catalysts were supported on AMC with 3%$H_3PO_4$ (40% actives). $HC/O_2/S$ employed was 1/0.55/15, at an LHSV of 1/5 (>98% butene-2 feed). All catalysts were reduced with $H_2$/steam at 550° C prior to run.

TABLE I

Oxidative Dehydrogenation of Butene-2 Over Lithium Ferrites[1]

| Example | Catalyst Li/Fe mole ratio | Calc. Temp. (° C) | Surf Area (m²/g) | $T_i$ (° C) | $T_{max}$ (° C) | Hours on Steam[2] | Results mole % C/S/$Y_{Bd.}$ |
|---|---|---|---|---|---|---|---|
| 1.[6] | 1/5 | 600 | 10.5 | 349 | 477 | 3½ | 59/95/56 |
|  |  |  |  | 357 | 505 | (3½)+5 | 58/94/55 |
| 2. | 1/5 | 700 | 8.1 |  |  | (4)+3) | —[3] |
| 3. | 1/5 | 550 | 11.7 | 361 | 533 | 3 | 59/93/55 |
|  |  |  |  | 250 | 485 | 4 | 60/94/56 |
| 4.[4] | 1/5 | 600 | 10.5 | 360 | 481 | 4½ | 62/94/58 |
| 5. | 1/5.5[5] | 600 | 3.6 | 402 | 458 | ½ | 41/95/89 |
|  |  |  |  | various |  | (1½+2) | —[3] |

[1] All catalysts were reduced with $H_2$/steam at 550° C prior to run.
[2] Hours on stream from previous day are indicated in parentheses. The system was left under $N_2$ at ~ 350° C overnight when run a second day.
[3] Unstable.
[4] Repeat of preparation used for Example 1.
[5] Excess Fe used as $FeCl_3$.
[6] Presence of lithium ferrite verified by X-ray analysis.

EXAMPLES 6 - 9

These examples demonstrate the criticality of the Li/Fe mole ratio. Catalyst preparation reactants and operating conditions were the same as in Examples 1 - 5. The difference being the mole ratios of Li/Fe. The data shows inferior catalyst in terms of yields at ratios of Li/Fe 2/5 and 1/7; however, within this range excellent catalysts are produced. The catalyst and results are set out in Table II.

TABLE II

| Ex. No. | Catalyst Li/Fe mole ratio | Calcination atmosphere | Temp. (° C) | Process Conditions $T_i$ (° C) | $T_{max}$ (° C) | Hours on Steam | Results mole % C/S/$Y_{Bd.}$ |
|---|---|---|---|---|---|---|---|
| 6.* | 2/5 | air | 600 | 410 | 535 | ¼ | 26/74/19 |
| 1.* | 1/5 | air | 600 | 349 | 477 | 3½ | 59/95/56 |
| 4. | 1/5 | air | 600 | 360 | 481 | 4½ | 62/94/58 |
| 7. | 1/5.5 | air | 600 | 355 | 482 | 3½ | 61/94/57 |
| 8. | 1/5.5 | $N_2$ | 600 | 326 | 470 | 3½ | 61/94/57 |
| 9. | 1/7 | air | 600 | 359 | 468 | 3½ | 41/94/39 |

*Presence of lithium ferrite verified by X-ray analysis.

EXAMPLES 10 - 19

These examples demonstrate that aluminum and chromium may be substituted for a portion of the iron in the present catalyst. The catalyst preparations were the same as examples 1 - 5, as were the conditions of the oxidation dehydrogenations. The aluminum substituted compositions are shown in Table III along with the results. The runs on chromium substituted lithium ferrite are set out in Table IV. Note the low inlet temperatures.

TABLE IV

OXIDATIVE DEHYDROGENATION OF BUTENE-2 OVER $Li_{0.5}Cr_xFe_{2.5-x}O_4$[1]

| Example No. | Catalysts mole % Cr[3] | "x" | Calc. Atm. | Process Conditions $T_i$ (° C) | $T_{max}$ (° C) | Approx. Hrs. on stream[2] | Results mole % C/S/$Y_{Bd.}$ |
|---|---|---|---|---|---|---|---|
| 13. | 40 | 1.0 | air | 200 | 442 | 4 | 50/91/46 |
| 14. | 40 | 1.0 | $N_2$ | 297 | 445 | 2½ | 53/94/50 |
| 15. | 20 | 0.5 | $N_2$ | 250 | 443 | (3½)+½ | 54/92/50 |
| 16. | 20 | 0.5 | air | 350 | 480 | ½ | 51/91/46 |
| 17. | 20 | 0.5 | air | 298 | 455 | 1 | 54/92/50 |
| 18. | 50 | 1.25 | $N_2$ | 244 | 415 | 2½ | 53/92/49 |
| 19. | 50 | 1.25 | air | 250 | 435 | 3 | 57/92/49 |

[1] Catalysts were prepared by calcining $Li_2C_2O_4/Fe_2O_3 . H_2O/Cr_2O_3 . xH_2O$ blends at 600° C for two hours in either air or $N_2$, 100 ml/min. for both), and were supported on AMC with 3 %$H_3PO_4$ (40 % actives), $HC/O_2/S$ ratio employed was 1/0.55/15, the LHSV was 1.5, and all catalysts were reduced with $H_2$/steam at 550° C prior to run.
[2] Hours on stream from previous day are indicated in parentheses. The system was left under $N_2$ at 250° C overnight.
[3] Based on Fe replaced.

EXAMPLES 20 - 22

These examples demonstrate the non-equivalence of sodium and potassium to lithium in the present catalyst. Copper of valence + 1 is also shown to be non-equivalent to + 1 valent lithium. The same slurry technique was used to produce the catalyst compositions, which were calcined in either air or nitrogen and deposited on 7 - 9 mesh alumina with 1.2% $H_3PO_4$ (unless otherwise indicated). The hydrocarbon feed was 98 + % butene-2 at the $HC/O_2/S$ ratio 1/0.55/15; LHSV 1.5. Table IV sets out the catalysts and the results.

TABLE V

| | | COMPARATIVE CATALYSTS COMPOSITION | | | | | | |
|---|---|---|---|---|---|---|---|---|
| | Catalysts | | Process Conditions | | | | Results | |
| Example No. | Composition mole ratio | Atmosp. | Temp° C | $T_f$(° C) | $T_{max}$(° C) | Hours on Steam | $C/S/Y_{Bd}$ | Remarks |
| 20. | LiNa ferrite[1] Li/Na/Fe-0.7/0.3/5 | air | 600 | 450 | — | 1½ | — | inactive |
| 21. | $K_2O.6Fe_2O_3$[2,3] K/Fe-1/6.6 | air | 900 | 450 | 530 | 2½ | — | low butene version 3½%$CO_2$, no butadiene |
| 22. | LiCu ferrite[4] Li/Cu/Fe-0.5/0.5/5 | $N_2$ | 600 | 342 | 490 | 2½ | 32/74/25 | poor selectivity |

*All catalyst were reduced with $H_2$/steam at 550° C prior to run.
[1]$Na_2CO_4$ used in slurry prep.
[2]$K_2CO_3$ used in slurry prep.
[3]K and Fe do not form a spinel analogons to Li-Fe, prep. suggested by U.S. Pat. No. 3,766,191.
[4]$Cu_2O$ used in slurry prep.

The invention claimed is:

1. A process for oxidative dehydrogenation comprising contacting oxygen and organic compounds having 2 to 20 carbon atoms, at least one

grouping and boiling point below about 350° C, in vapor phase at a temperature of at least about 250° C in the presence of a catalyst composition containing a lithium ferrite consisting essentially of lithium, iron and oxygen; lithium, iron oxygen and aluminum or chromium; or lithium, iron, oxygen, aluminum and chromium the mole ratio of lithium to iron being in the range between 2:5 to 1:7, said catalyst composition having a surface area of at least 8.1 m²/gram.

2. The process according to claim 1 wherein aluminum or chromium may comprise up to 48 mole % of the total of iron, aluminum or chromium present in said catalyst.

3. The process according to claim 2 wherein the aluminum or chromium may comprise up to about 40 mole % of the total of iron, aluminum or chromium.

4. The process according to claim 1 wherein the mole ratio of lithium to iron is in the range of 1:4 to 1:6.

5. The process according to claim 1 wherein said organic compounds comprise hydrocarbons.

6. The process according to claim 1 wherein a product is recovered, corresponding to said organic compounds and having a higher degree of ethylenic unsaturation than said organic compounds.

7. The process according to claim 1 wherein said catalyst composition consists essentially of lithium, iron and oxygen.

8. The process according to claim 1 wherein said catalyst composition consists essentially of lithium, iron, oxygen and aluminum or chromium.

9. The process according to claim 8 wherein said catalyst composition consists essentially of lithium, iron, oxygen and aluminum.

10. The process according to claim 8 wherein said catalyst composition consists essentially of lithium, iron, oxygen and chromium.

11. The process according to claim 1 wherein the catalyst composition has a surface area of at least 10.5 m²/gram.

* * * * *